United States Patent
Yamauchi et al.

(10) Patent No.: US 6,313,315 B1
(45) Date of Patent: Nov. 6, 2001

(54) METHODS FOR PRODUCING N-PROTECTED-AZETIDINE-2-CARBOXYLIC ACIDS

(75) Inventors: Kazuhiro Yamauchi, Ibaraki; Hideki Ushio, Takatsuki; Isao Kurimoto, Suita, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/584,853

(22) Filed: Jun. 1, 2000

(30) Foreign Application Priority Data

Jun. 1, 1999  (JP) ................................. 11-153752

(51) Int. Cl.$^7$ ................................. C07D 205/04
(52) U.S. Cl. ................................. 548/953
(58) Field of Search ................................. 548/953

(56) References Cited

U.S. PATENT DOCUMENTS 5,880,291   3/1999   Ushio et al. .

FOREIGN PATENT DOCUMENTS

| 0855446 | 7/1998 | (EP) . |
| 0957089 | 11/1999 | (EP) . |
| 0974670 | 1/2000 | (EP) . |
| WO9702241 | 1/1997 | (WO) . |
| WO9802568 | 1/1998 | (WO) . |
| WO9850420 | 11/1998 | (WO) . |
| WO0012473 | 3/2000 | (WO) . |

Primary Examiner—Joseph K. McKane
Assistant Examiner—Sonya N. Wright
(74) Attorney, Agent, or Firm—Birch, Stewart, Kolasch & Birch, LLP

(57) ABSTRACT

There is disclosed a method for producing an essentially enantiomerically pure N-protected-azetidine-2-carboxylic acid of formula (1):

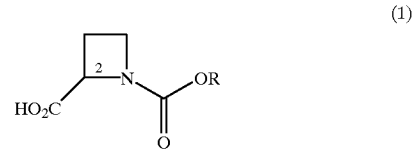

(1)

which method is characterized by:

subjecting a crude enantiomerically excess N-protected-azetidine-2-carboxylic acid comprising said enantiomer represented by formula (1) in excess to the other enantiomer thereof to crystallization in an organic solvent selected from aromatic hydrocarbon, aliphatic ether, aliphatic alcohol, aliphatic ketone, aliphatic nitrile, aliphatic amide, aliphatic sulfoxide, aliphatic ester and a mixed solvent thereof, wherein R is:
- an optionally substituted alkyl, alicyclic or alicyclicalkyl group,
- an optionally substituted alkenyl group,
- an optionally substituted aryl group,
- an optionally substituted heteroaryl group, or
- a dialkylamino group, and
- absolute configuration of the asterisked asymmetric carbon atom is S or R.

9 Claims, No Drawings

METHODS FOR PRODUCING N-PROTECTED-AZETIDINE-2-CARBOXYLIC ACIDS

BACKGROUND OF THE INVENTION

1. Field of the Invention

The present invention relates to a process for producing an optically active N-protected-azetidine-2-carboxylic acid, which is a useful starting material for producing pharmaceuticals as described, for example, in WO98/50420 or Brain Res., 801 (1–2), p. 158, 1998.

2. Description of Related Art

Enantiomerically pure N-protected-azetidine-2-carboxylic acid such as (S)-N-benzoylazetidine-2-carboxylic acid has been produced by recrystallizing (S)-N-benzoylazetidine-2-carboxylic acid(94% e.e.) as disclosed in WO98/02568. For further derivatization to enantiomerically pure azetidine-2-carboxylic acid or a peptide, however, said compound required cumbersome alkaline hydrolysis and neutralization steps or further step of introducing a suitable protective group.

SUMMARY OF THE INVENTION

An object of the invention is to provide a method for purifying azetidine-2-carboxylic acid, which method can conveniently produce an enantiomerically pure azetidine-2-carboxylic acid with a suitable N-protective group.

The present invention provides:

a method for producing an essentially enantiomerically pure N-protected-azetidine-2-carboxylic acid of formula (1):

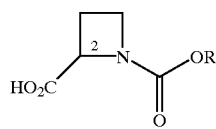

(1)

which method comprises:

subjecting a crude enantiomerically excess N-protected-azetidine-2-carboxylic acid comprising said enantiomer represented by formula (1) in excess to the other enantiomer thereof to crystallization in an organic solvent selected from aromatic hydrocarbon, aliphatic ether, aliphatic alcohol, aliphatic ketone, aliphatic nitrile, aliphatic amide, aliphatic sulfoxide, aliphatic ester and a mixed solvent thereof, wherein R is:

an optionally substituted alkyl, alicyclic or alicyclicalkyl group, an optionally substituted alkenyl group, an optionally substituted aryl group, an optionally substituted heteroaryl group, or a dialkylamino group, and absolute configuration of the asterisked asymmetric carbon atom is S or R.

DESCRIPTION OF THE PREFERRED EMBODIMENTS

In the present invention, the term "essentially enatiomerically pure" means an enantiomeric excess (% e.e.) of approximately 98% e.e. or higher. Such compounds can be advantageously used for preparing pharmaceuticals or pesticides without further purification.

The crude enantiomerically excess N-protected-azetidine-2-carboxylic acid to be purified by the present method comprises enantiomer of formula (1) in excess to the other enantiomer thereof The enantiomer of formula (1) will be explained below.

The optionally substituted alkyl group for R in formula (1) include an alkyl, alicyclic or alicyclicalkyl group having 1 to 13 carbon atoms, which may be substituted.

Said optionally substituted alkyl, alicyclic or alicyclicalkyl group may be substituted with at least one group selected from:
a cyano group, a halogen atom, a tri(C1–C4)alkylsilyl group,
a (C1–C4)alkylthio group,
a (C1–C4)alkysulfinyl group,
a (C1–C4)alkylsulfonyl group,
a phosphonio group substituted with groups selected from a (C1–C4)alkyl and phenyl group,
wherein the (C1–C4)alkyl groups may be bonded at their terminals to form a ring, and
a (C6–C14)aryl, (C6–C14)arylsulfonyl, (C7–C15) arylcarbonyl, (C4–C13)heteroaryl group, wherein said aryl or heteroaryl group may be substituted with at least one group selected from:
a (C1–C4)alkyl group, a halogen atom, an amino group,
a nitro group, a (C1–C4)alkoxy group,
a (C1–C4)alkylsulfinyl group and a sulfonic group.

In the above-described definition, the halogen atom means a fluorine atom, a chlorine atom, a bromine atom or an iodine atom.

Examples of the (C1–C4)alkyl groups described above include a methyl group, an ethyl group, an i-propyl group, a n-propyl group, a n-butyl group, an i-butyl group, sec-butyl group and t-butyl group.

Examples of the (C1–C4)alkoxy groups include a methoxy group, an ethoxy group, an i-propoxy group, a n-propoy group, a n-butoxy group, an i-butoxy group, sec-butoxy group and t-butoxy group.

Examples of the (C6–C14)aryl groups include a phenyl group, a naphthyl group, an anthranyl group and a biphenyl group.

Examples of the (C4–C13)heteroaryl group include a 2,3-, and 4-pyridyl group, a 2,7-di-t-butyl-9-(10,10-dioxo-10,10, 10,10-tetrahydrothioxanthyl) group, a quinolyl group such as 8-quinolyl group.

Examples of the alkyl, alicyclic or alicyclicalkyl group having 1 to 13 carbon atoms include methyl, ethyl, isobutyl, t-butyl, 1-adamantyl, 1-(1-adamantyl)-1-methylethyl and the like.

Examples of the alkyl group which may be substituted with a (C6–C14)aryl group which may be substituted include benxyl, p-methoxybenzyl, p-nitrobenzyl, p-bromobenzyl, 4-methylsulfinylbenzyl, 2,4-dichlorobenzyl, 2-phenylethyl, 9-fluorenylmethyl, 9-(2-sulfo)fluorenylmethyl, 9-(2,7-dibromo)fluorenylmethyl, 1-methyl-1-(4-biphenylyl)ethyl, 1-(3,5-di-t-butylphenyl)-1-methylethyl, 9-anthranylmethyl, diphenylmethyl and the like.

Examples of the alkyl group substituted with a cyano group include 1,1-dimethyl-2-cyanoethyl.

Examples of the alkyl group substituted with a halogen atom include trichloroethyl, 1,1-dimethyl-2-chloroethyl, 1,1-dimethyl-2,2-dibromoethyl and 1,1-dimethyl-2,2,2,-trichloroethyl.

Examples of the alkyl group substituted with arylcarbonyl group, which aryl group may be substituted, include a methoxyphenacyl group.

Examples of the alkyl group substituted with said silyl group include a trimethylsilylethyl group.

Examples of the alkyl group substituted with the alkylthio group include 2-methylthioethyl and [2-(1,3-dithianyl)]methyl.

Examples of the alkyl group substituted with the alkylsulfonyl or arylsulfonyl group include 2-methylsulfonylethyl and 2-(p-toluenesulfonyl)ethyl.

Examples of the alkyl group substituted with the phosphonio group include 2-trimethylphosphonioethyl and 2-triphenylphosphonioisopropyl.

Examples of the alkyl group substituted with the hetroaryl group include 2-(2'-pyridyl)ethyl group, 2,7-di-t-butyl-9-(10,10-dioxo-10,10,10,10-tetrahydrothioxanthyl)methyl or the like.

The optionally substituted alkenyl group for R include a (C2–C6)alkenyl group which may be substituted with a phenyl or nitrophenyl group such as vinyl, allyl, 1-isopropylallyl, cinnamyl and 4-nitrocinnamyl.

The optionally substituted aryl group for R include a phenyl group which may be substituted with at least one methylthio group such as phenyl, 4-methylthiophenyl or 2,4-dimethylthiophenyl.

The optionally substituted heteroaryl group for R include a (C5–C9)heteroaryl group such as a pyridyl group or a quinolyl group (e.g., 8-quinolyl).

The dialkylamino group for R include a di(C1–C6)alkylamino group, wherein said alkyl groups may be bonded each other at their terminals to form a ring such as piperidinyl and the like.

Preferred R group includes the optionally substituted alkyl group, more preferred groups include t-butyl, 9fluorenylmethyl, benzyl and the like.

Specific examples of the compound of formula (1) include following compounds in which the configuration of the asterisked asymmetric carbon atom is R or S:

N-methyloxycarbonyl-azetidine-2-carboxylic acid,
N-ethyloxycarbonyl-azetidine-2-carboxylic acid,
N-isobutyloxycarbonyl-azetidine-2-carboxylic acid,
N-t-butyloxycarbonyl-azetidine-2-carboxylic acid,
N-(1-adamantyl)oxycarbonyl-azetidine-2-carboxylic acid,
N-[1-(1-adamantyl)-1-methylethyl]oxycarbonyl-azetidine-2-carboxylic acid,
N-benzyloxycarbonyl-azetidine-2-carboxylic acid,
N-(p-methoxybenzyloxycarbonyl)-azetidine-2-carboxylic acid,
N-(p-nitrobenzyloxycarbonyl)-azetidine-2-carboxylic acid,
N-(p-bromobenzyloxycarbonyl)-azetidine-2-carboxylic acid,
N-(4-methylsulfinylbenzyloxycarbonyl)-azetidine-2-carboxylic acid,
N-(2,4-dichlorobenzyloxycarbonyl)-azetidine-2-carboxylic acid,
N-(2-phenylethyloxycarbonyl)-azetidine-2-carboxylic acid,
N-(9-fluorenylmethyloxycarbonyl)-azetidine-2-carboxylic acid,
N-[9-(2-sulfo)fluorenylmethyloxycarbonyl]-azetidine-2-carboxylic acid,
N-[9-(2,7-dibromo)fluorenylmethyloxycarbonyl]-azetidine-2-carboxylic acid,
N-[2,7-di-t-butyl-[9-(10,10-dioxo-10,10,10,10-tetrahydrothioxanthyl)-methyloxycarbonyl]-azetidine-2-carboxylic acid,
N-[1-methyl-1-(4-biphenylyl)ethyloxycarbonyl]-azetidine-2-carboxylic acid,
N-[1-(3,5-di-t-butylphenyl)-1-methylethyloxycarbonyl]-azetidine-2-carboxylic acid,
N-(9-anthranylmethyloxycarbonyl)-azetidine-2-carboxylic acid,
N-diphenylmethyloxycarbonyl-azetidine-2-carboxylic acid,
N-[(1,1-dimethyl-2-cyanoethyl)oxycarbonyl]-azetidine-2-carboxylic acid,
N-trichloroethyloxycarbonyl-azetidine-2-carboxylic acid,
N-(1,1-dimethyl-2-chloroethyloxycarbonyl)-azetidine-2-carboxylic acid,
N-(1,1-dimethyl-2,2-dibromoethyloxycarbonyl)-azetidine-2-carboxylic acid,
N-(1,1-dimethyl-2,2,2-trichloroethyloxycarbonyl)-azetidine-2-carboxylic acid,
N-methoxyphenacyloxycarbonyl-azetidine-2-carboxylic acid,
N-trimethylsilylethyloxycarbonyl-azetidine-2-carboxylic acid,
N-(2-methylthioethyloxycarbonyl)-azetidine-2-carboxylic acid,
N-(2-methylsulfonylethyloxycarbonyl)-azetidine-2-carboxylic acid,
N-[2-(1,3-dithianyl)]methyloxycarbonyl)-azetidine-2-carboxylic acid,
N-[2-(p-toluenensulfonyl)ethyloxycarbonyl]-azetidine-2-carboxylic acid,
N-(2-trimethylphosphonioethyloxycarbonyl)-azetidine-2-carboxylic acid,
N-(2-triphenylphosphonioisopropyloxycarbonyl)-azetidine-2-carboxylic acid,
N-[2-(2'-pyridyl)ethyloxycarbonyl]-azetidine-2-carboxylic acid,
N-vinyloxycarbonyl-azetidine-2-carboxylic acid,
N-allyloxycarbonyl-azetidine-2-carboxylic acid,
N-(1-isopropylallyloxycarbonyl)-azetidine-2-carboxylic acid,
N-cinnamyloxycarbonyl-azetidine-2-carboxylic acid,
N-(4-nitrocinnamyloxycarbonyl)-azetidine-2-carboxylic acid,
N-phenyloxycarbonyl-azetidine-2-carboxylic acid,
N-(4-methylthiophenyloxycarbonyl)-azetidine-2-carboxylic acid,
N-(2,4-dimethylthiophenyloxycarbonyl)-azetidine-2-carboxylic acid,
N-(8-quinolyloxycarbonyl)-azetidine-2-carboxylic acid,
N-[(1-piperidinyl)oxycarbonyl]-azetidine-2-carboxylic acid and the like.

Examples of the organic solvent include:

an aromatic hydrocarbon(e.g., (C6–C8) aromatic hydrocarbon which may be substituted with a halogen atom) such as benzene, toluene, ethylbenzene, xylene or chlorobenzene, an aliphatic ether (e.g., (C4–C6) aliphatic ether) such as t-butylmethylether, isopropylether, tetrahydrofuran or dioxane, an aliphatic ester (e.g., (C4–C6) aliphatic ester) such as ethyl acetate, butyl acetate or isopropyl acetate an aliphatic alcohol (e.g., (C1–C4) aliphatic alcohol) such as methanol, ethanol, isopropanol, n-ethanol or t-butanol, an aliphatic ketone (e.g., (C3–C6) aliphatic ketone) such as acetone, 2-butanone, methyl isopropyl ketone or methyl isobutyl ketone an aliphatic nitrile (e.g., (C2–C4) aliphatic nitrile) such as acetonitrile, propionitrile or butyronitrile an aliphatic amide (e.g., N,N-dimethyl(C1–C2) acylamide) such as N,N-dimethylformamide or N,N-dimethylacetamide, an aliphatic sulfoxide such as dimethylsulfoxide.

The solvent may be employed alone or as a mixture of two or more thereof.

The aromatic hydrocarbon is preferably employed, and toluene and a mixed solvent thereof with other solvents are more preferred.

The amount of the solvent to be used is not particularly limited but may be set by taking account of the amount of the crude enantiomerically excess N-protected-azetidine-2-carboxylic acid comprising compound of formula (1) in excess to the other enantiomer thereof and the kind of the solvent and is, for example, about 0.1 to 100 parts by weight, preferably 0.5 to 50 parts by weight per 1 part by weight of said crude N-protected-azetidine-2-carboxylic acid.

The crude enantiomerically excess N-protected-azetidine-2-carboxylic acid may be obtained by a conventional chemical or enzymatic resolution and the like. The crude enantiomerically excess N-protected-azetidine-2-carboxylic acid with about 80% e.e. or higher is preferably used in the present method.

The crude N-protected-azetidine-2-carboxylic acid is usually subjected to crystallization by decreasing the temperature of a solution of the crude compound in the organic solvent as described above. The crystallization may be conducted in the copresence of a bad solvent. Examples of the bad solvent includes an aliphatic or alicyclic hydrocarbon solvent (e.g., (C6–C8) aliphatic or alicyclic hydrocarbon) such as n-hexane, heptane, cyclohexane or isooctane, which may be added to the solution of the crude compound before precipitation of the desired crystals, or may be dropwise added to the precipitating crystallization solution. A seed crystal may be also added to the solution in order to induce precipitation of the crystals.

The crystallization is conducted usually at a temperature range of between −50° C. to 200° C., preferably −20° C. to 150° C., more preferably −20° C. to 100° C. The temperature is not particularly restricted and may be optionally set based on the amount and kind of the solvent to be used.

After the crystallization, precipitated crystals may be collected by a conventional method such as a filtration. If necessary, the collected crystal may be washed with water, the organic solvent as described above for crystallization or bad solvent as described above.

An essentially enatiomerically pure N-protected-azetidine-2-carboxylic acid (1) thus obtained may be subjected to a subsequent reaction as it is, or may be deprotected, if necessary, to give an essentially optically pure azetidine-2-carboxylate or its salt.

Typically, the deprotection of the above-described N-protecting group can be conducted by reacting the crystallized compound under an acidic condition by using hydrochloric acid, sulfuric acid, trifluoroacetic acid or the like in water or an organic solvent, and heating if necessary.

Alternatively, the deprotection reaction can be conducted by the following typical methods or may be conducted by those methods as disclosed in the reference below.

When R is, for example, allyl, benzyl, p-nitrobenzyl, 2,4-dichlorobenzyl, cinnamyl, 9-anthranymethyl or diphenylmethyl group, removal of the protecting group is usually conducted by reacting such a compound in the presence of a catalyst, with a reducing agent to produce the enantiomerically pure azetidine-2-carboxylic acid.

The catalyst may be, for example, noble metal catalysts usually employed in a catalytic hydrogenation reaction, more specifically palladium, palladium acetate, palladium chloride, palladium oxide, palladium hydroxide and the like, which may be supported on activated carbon, alumina and the like. The amount of the catalyst to be used is usually within a range of from 0.0001 to 0.5 part by weight per 1 part by weight of the essentially enantiomerically pure N-protected azetidine-2-carboxylic acid.

Examples of the reducing agent include hydrogen, hydrazine and a salt thereof such as a hydrochloride, a sulfate, an acetate and the like, and formic acid and an ammonium salt thereof.

The reaction is usually carried out in a solvent. Examples of the solvent include: water, an alcohol solvent such as methanol, ethanol and 2-propanol, an ester solvent such as ethyl acetate, methyl acetate and butyl acetate, a nitrile solvent such as acetonitrile, an aromatic hydrocarbon solvent such as toluene, xylene and benzene, an aliphatic hydrocarbon solvent such as hexane and heptane, a halogen-containing hydrocarbon solvent such as dichloromethane, dichloroethane, chloroform, chlorobenzene and orthodichlorobenzene, an ether solvent such as diethyl ether, isopropyl ether and t-butyl methyl ether, an amide solvent such as acetamide, N, N-dimethyl formamide and N, N-dimethylacetamide. These solvents may be used alone or in combination of two or more. The amount of the solvent to be used is usually within a range of from 2 to 100 parts by weight per part by weight of the essentially enantiomerically pure N-substituted azetidine-2-carboxylic acid compound represented by the formula (1).

When hydrogen is employed as a reducing agent, for example, a catalyst and the crystallized essentially enantiomerically pure N-protected azetidine-2-carboxylic acid compound of formula (1) are usually added to a solvent, and a hydrogen gas is thereafter supplied into the reaction system. The supply of the hydrogen gas may be carried out by passing the gas through the reaction system or the reaction system may be stirred under a hydrogen gas atmosphere at normal pressure or compressed pressure.

When a reducing agent other than hydrogen is employed, for example, the essentially enantiomerically pure N-protected azetidine-2-carboxylic acid compound of formula (1) and a catalyst may be added to a solvent and the reducing agent may thereafter be added to the mixture.

The reaction temperature is usually within a range of from −50° C. to 200° C., preferably from 0° C. to 150° C.

When R is an allyl group in the N-substituted azetidine-2-carboxylic acid compound of formula (1), the deprotected compound can be obtained, for example, by using tri-n-butyltin hydride, acetic acid and the like in the presence of a catalyst such as tetrakis(triphenylphosphine)palladium.

The deprotection may also be performed according to a known method such as that described in "Protective Groups in Organic Synthesis" (T. W. Greene, P. G. M. Wuts, 1991, John Willey & Sons, Inc.), the whole disclosure of which is incorporated herein by reference.

The crude enantiomerically excess N-protected-azetidine-2-carboxylic acid can be obtained by introducing a N-protecting group of formula: ROCO, wherein R has the same meaning as defined above, to a crude enantiomerically excess azetidine-2-carboxylic acid according to a method as described in "Protective Groups in Organic Synthesis" (T. W. Greene, P. G. M. Wuts, 1991, John Willey & Sons, Inc.) and the like.

Said introduction of the protecting group may be carried out by reacting crude enatiomeric excess azetidine-2-carboxylic acid with a protective reagent of formula ROCO-L, wherein L represents a leaving group, in the presence of a base.

Examples of the leaving group "L" include a halogen atom, ROCOO, succinimidyloxy group and the like.

For example, t-butoxycarbonyl group can be introduced by using di-t-butyldicarbonate according to a known method.

Alternatively, the crude enantiomerically excess azetidine-2-carboxylic acid which contains N-protected-azetidine-2-carboxylic acid of formula (1) in excess to the other enantiomer may be produced by a conventional chemical or enzymatic resolution.

According to the invention, an essentially optically pure N-protected-azetidine-2-carboxylic acid can readily and efficiently be produced by crystallizing a crude enantiomerically excess N-protected-azetidine-2-carboxylic acid, which contains one of its isomers in excess, from an organic solvent.

EXAMPLES

The present invention is further described in the following examples, which are not to be construed to limit the invention thereto.

Example 1

161.4 g of an aqueous solution containing (S)-azetidine-2-carboxylic acid having 94.6% e.e. (azetidine-2-carboxylic acid content: 20.0 g, 198 mmol) was combined with a 64% by weight toluene solution of di-t-butyldicarbonate (di-t-butyldicarbonate: 56.1 g, 257 mmol) and then treated dropwise with 38.1 g of a 27% aqueous solution of sodium hydroxide (sodium hydroxide: 10.8 g, 257 mmol) and stirred at 40° C. for 4 hours. After the reaction, 80.0 g of toluene was added and the mixture was stirred for 30 minutes and then allowed to stand to separate the phases to obtain 230.0 g of an aqueous layer (N-t-butyloxycarbonyl-azetidine-2-carboxylic acid content: 38.9 g, 193 mmol). 222.3 g of this aqueous layer (N-t-butyloxycarbonyl-azetidine-2-carboxylic acid content: 37.6 g, 187 mmol) was combined with 35.0 g of sodium chloride, treated dropwise with 26.9 g of a 36% hydrochloric acid, and then extracted twice with 75.0 g of toluene. The toluene layer was washed with a 20 (w/w)% aqueous sodium chloride solution, settled and separated to give 194.4 g of a toluene solution of N-t-butyloxycarbonyl-azetidine-2-carboxylic acid (N-t-butyloxycarbonyl-azetidine-2-carboxylic acid content: 37.2 g, 185 mmol). The (S)-N-t-butyloxycarbonyl-azetidine-2-carboxylic acid thus obtained showed 94.6% e.e.

Subsequently, a 177.9 g of this toluene solution (N-t-butyloxycarbonyl-azetidine-2-carboxylic acid content: 34.0 g, 169 mmol) was evaporated under reduced pressure at 60° C. to distill the solvent, and concentrated to 69.4 g (N-t-butyloxycarbonyl-azetidine-2-carboxylic acid concentration: 49.0% by weight). While keeping the concentration at 60° C., 0.15 g of a seed crystal was added and the mixture was stirred for 1 hour and then cooled to 0° C. at the cooling rate of 20° C./h. The crystal which was precipitated was filtered, washed with 20.0 g of a cooled toluene and dried to give 30.3 g of (S)-N-t-butyloxycarbonyl-azetidine-2-carboxylic acid (crystallization yield: 86.6%), of which HPLC analysis on a chiral column showed 99.6% e.e.

Example 2

5.00 g of (S)-N-t-butyloxycarbonyl-azetidine-2-carboxylic acid (99.6% e.e.) obtained in a similar manner as in Example 1 was added to 53 g of a 17% solution of hydrogen chloride in ethyl acetate and stirred for 1 hour. The reaction mixture was concentrated under reduced pressure to give 3.45 g of (S)-azetidine-2-carboxylic acid hydrochloride. The yield was 100%, and an HPLC analysis of the salt on a chiral column showed 99.6% e.e.

What is claimed is:

1. A method for producing an essentially enantiomerically pure N-protected-azetidine-2-carboxylic acid of formula (1):

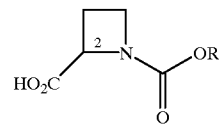

(1)

which method comprises:
  subjecting a crude enantiomerically excess N-protected-azetidine-2-carboxylic acid comprising said enantiomer represented by formula (1) in excess to the other enantiomer thereof to crystallization in an organic solvent selected from aromatic hydrocarbon, aliphatic ether, aliphatic alcohol, aliphatic ketone, aliphatic nitrile, aliphatic amide, aliphatic sulfoxide, aliphatic ester and a mixed solvent thereof,
  wherein R is
    an optionally substituted alkyl, alicyclic or alicyclicalkyl group,
    an optionally substituted alkenyl group,
    an optionally substituted aryl group,
    an optionally substituted heteroaryl group, or
    a dialkylamino group, and
    absolute configuration of the asterisked asymmetric carbon atom is S or R.

2. A method according to claim 1, wherein
  said organic solvent is an organic solvent selected from (C6–C8)aromatic hydrocarbon, (C4–C6)aliphatic ether,
    (C1–C4)aliphatic alcohol, (C3–C6)aliphatic ketone,
    (C2–C4)aliphatic nitrile, N,N-dimethyl(C1–C2) acylamide, dimethylsulfoxide, and (C4–C6)aliphatic ester, and
  R is
    an alkyl, alicyclic or alicyclicalkyl group having 1 to 13 carbon atoms, which may be substituted with
  at least one group selected from:
    a cyano group, a halogen atom, a tri(C1–C4)alkylsilyl group,
    a (C1–C4)alkylthio group,
    a (C1–C4)alkylsulfinyl group,
    a (C1–C4)alkylsulfonyl group,
    a phosponio group substituted with groups selected from a (C1–C4)alkyl and phenyl group,
  wherein the (C1–C4)alkyl groups may be bonded at their terminals to form a ring, and
  a (C6–C14)aryl, (C6–C14)arylsulfonyl, (C7–C15) arylcarbonyl, (C4–C13)heteroaryl group, wherein said aryl or heteroaryl group may be substituted with at least one group selected from:
    a (C1–C4)alkyl group, a halogen atom, an amino group,
    a nitro group, a (C1–C4)alkoxy group,
    a (C1–C4)alkylsulfinyl group and a sulfonic group,
  a (C2–C6)alkenyl group which may be substituted with a phenyl or nitrophenyl group,
  a phenyl group which may be substituted with at least one methylthio group, a (C5–C9)heteroaryl group, or a di(C1–C6)alkylamino group, wherein said alkyl groups may be bonded each other at their terminals to form a ring.

3. A method according to claim 1 or 2, wherein R in the formula (1) represents a t-butyl, 9-fluorenyl or benzyl group.

4. A method according to claim 1 or 2, wherein R in the formula (1) represents a t-butyl group.

5. A method according to claim 1, wherein said organic solvent is aromatic hydrocarbon.

6. A method according to claim 1, wherein said organic solvent is toluene or a mixted solvent thereof.

7. A method according to claim 1 or 2, wherein the crude enantiomerically excess N-protected-azetidine-2-carboxylic acid is obtained by reacting a protective reagent of formula ROCO-L, wherein R has the same meaning as defined in claim 1 and L is a leaving group in the presence of a base with a crude enantiomerically excess azetidine-2-carboxylic acid which contains one of its enantiomer of formula (1) in excess.

8. A method according to any of claim 1, which further comprises deprotecting the essentially enantiomerically pure N-protected-azetidine-2-carboxylic acid of formula (1) to produce an essentially enantiomerically pure azetidine-2-carboxylic acid or its salt.

9. A method according to claim 1 or 2, wherein said crystallization is conducted in the copresence of a bad solvent.

* * * * *